United States Patent [19]

Kojima et al.

[11] Patent Number: 4,757,087
[45] Date of Patent: Jul. 12, 1988

[54] CARBACYCLIN DERIVATIVES

[75] Inventors: Koichi Kojima; Shinsaku Kobayashi, both of Hiromachi, Japan

[73] Assignee: Sankyo Company Limited, Tokyo, Japan

[21] Appl. No.: 840,920

[22] Filed: Mar. 18, 1986

[30] Foreign Application Priority Data

Mar. 19, 1985 [JP] Japan .................. 60-55305

[51] Int. Cl.⁴ .................. C07C 62/32; A61K 31/21
[52] U.S. Cl. .................. 514/510; 560/119; 562/501
[58] Field of Search .................. 560/119; 562/501; 514/510, 557, 925

[56] References Cited

U.S. PATENT DOCUMENTS 4,238,414 12/1980 Morton, Jr. .................. 560/119 X
4,338,457 7/1982 Aristoff .................. 560/119
4,628,110 12/1986 Aristoff .................. 560/119

FOREIGN PATENT DOCUMENTS 2012265 7/1979 United Kingdom .

OTHER PUBLICATIONS

The American Heritage Dictionary, Second college edition, Houghton Mifflin Company, U.S.A., 1982, p. 81.
Brodie and Chase, Gastroenterology, vol. 53, No. 4 – "Role of Gastric Acid in Aspirin-Induced Gastric Irritation in the Rat".

Primary Examiner—Michael L. Shippen
Attorney, Agent, or Firm—Frishauf, Holtz, Goodman & Woodward

[57] ABSTRACT

Carbacyclin derivatives with anti-ulcer activity comprise compounds of the general formula (I):

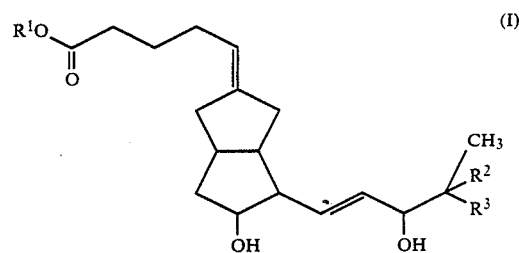

(wherein $R^1$ is selected from the group consisting of a hydrogen atom and an alkyl group having from 1 to 10 carbon atoms; $R^2$ is selected from the group consisting of a hydrogen atom and a methyl group; and $R^3$ is selected from the group consisting of a 3-butenyl group, a 4-pentenyl group and a 5-methyl-4-hexenyl group), and pharmaceutically acceptable salts thereof.

29 Claims, No Drawings

CARBACYCLIN DERIVATIVES

BACKGROUND OF THE INVENTION

This invention relates to carbacyclin derivatives, and in particular to carbacyclin derivatives with anti-ulcer action.

Carbacyclin derivatives share in common the carbacyclin structure which is of the formula (A):

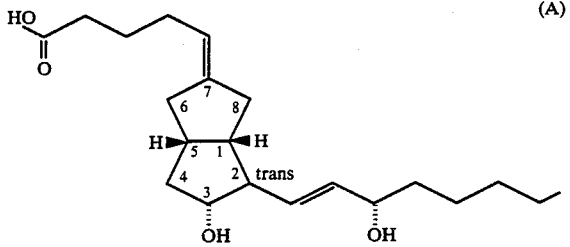

Carbacyclin and its derivatives are chemically stable and have various physiological effects, including inhibition of blood platelet aggregation (GB Patent Specification No. 2012265A, U.S. Pat. No. 4,238,414).

Compounds such as those of formula (B) below are now being developed as therapeutic agents for treatment of thrombosis.

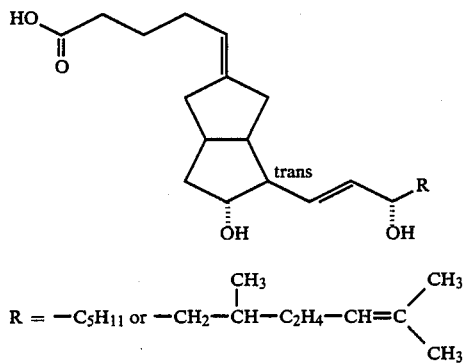

$$R = -C_5H_{11} \text{ or } -CH_2-\overset{CH_3}{\underset{|}{CH}}-C_2H_4-CH=C\overset{CH_3}{\underset{CH_3}{\diagdown}}$$

More generally, the literature such as GB Patent Specification No. 2012265A, U.S. Pat No. 4,238,414 and U.S. Pat. No. 4,338,457 disclose that compounds of the formula (B), wherein the group R is an alkenyl group, have a variety of actions, including inhibition of blood platelet aggregation, anti-ulcer activity, inhibition of gastric juice secretion, and bronchodilatory activity.

OBJECTS OF THE INVENTION

The present invention is concerned with the discovery of new and useful activity in carbacyclin derivatives. A related object is the discovery of novel carbacyclin derivatives.

SUMMARY OF THE INVENTION

The present invention provides carbacyclin derivatives with pharmacologically useful activity, especially anti-ulcer action.

The carbacyclin derivatives of this invention are compounds of the general formula (I):

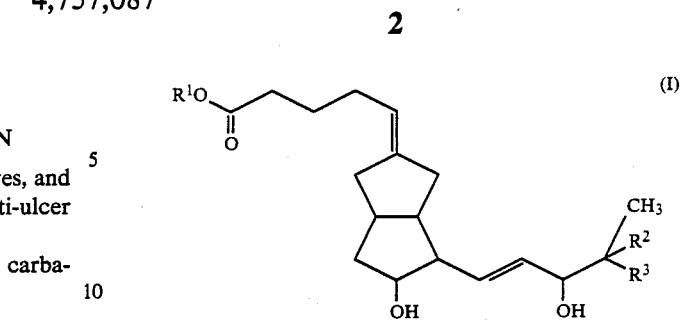

(wherein $R^1$ represents a hydrogen atom or an alkyl group having from 1 to 10 carbon atoms; $R^2$ represents a hydrogen atom or a methyl group; and $R^3$ represents a 3-butenyl group, a 4-pentenyl group or a 5-methyl-4-hexenyl group).

The carbacyclin derivatives of this invention further include the pharmaceutically acceptable salts of the compounds of formula (I).

The present invention further embraces pharmaceutical compositions of the carbacyclinc derivatives of the invention, particularly in view of their potent anti-ulcer activity. The anti-ulcer activity of the carbacyclin derivatives of this invention is particularly remarkably when compared with the structurally similar compounds which are disclosed in the state of the art and which are of the formula (B) given above wherein the group R is 2-pentenyl, 2,6-dimethyl-5-heptenyl, or the like.

It is to be noted that the compounds of this invention which are compounds of the general formula (I) wherein the group $R^2$ is methyl also weakly exhibit other physiological effects shown by known carbacyclin derivatives, such as inhibition of blood platelet aggregation.

The use of the carbacyclin derivatives of this invention in the treatment of ulcers is also part of the instant invention, along with processes for preparing the carbacyclin derivatives.

PREFERRED EMBODIMENTS OF THE INVENTION

Examples of an alkyl group for the group $R^1$ include a methyl, ethyl, n-propyl, isopropyl, n-butyl, n-pentyl, n-hexyl, n-heptyl, n-octyl, n-nonyl or n-decyl group, with a methyl group being particularly preferred.

Preferred compounds of formula (I) include those compounds wherein $R^1$ is a hydrogen atom or a methyl group, and $R^2$ and $R^3$ as are defined. Other preferred compounds of formula (I) include those compounds wherein $R^2$ is a methyl group, and $R^1$ and $R^3$ are as defined. Also preferred compounds of formula (I) include those compounds wherein $R^3$ is a 3-butenyl or 4-pentenyl group, and $R^1$ and $R^2$ are as defined. Especially preferred compounds are those compounds wherein $R^2$ is a methyl group, and those compounds wherein $R^3$ is a 3-butenyl or 4-pentenyl group, more particularly a 4-pentenyl group.

Examples of the pharmacologically acceptable salts of this invention include an alkali metal or alkaline earth metal salt, such as a sodium, potassium, magnesium or calcium salt; an ammonium salt; a quaternary ammonium salt, such as a tetramethylammonium, tetraethylammonium, benzyltrimethylammonium or phenyltriethylammonium salt; a salt with an aliphatic, alicyclic or araliphatic amine, such as a salt with methylamine, ethylamine, dimethylamine, diethylamine, trimethylamine, triethylamine, N-methylhexlamine, cyclopentylamine, dicyclohexylamine, benzylamine, α-phenylethylamine or ethylenediamine; a salt with a heterocyclic amine or alkylheterocyclic amine, such as a salt with piperidine, morpholine, pyrrolidine, piperazine, pyridine, 1-methylpiperazine or 4-ethylmorpholine; or a salt with an amine substituted with a hydrophilic radical, such as a salt with monoethanolamine, ethyldiethanolamine or 2-amino-1-butanol.

If desired, a carbocyclic derivative of this invention can be used in the form of a clathrate compound with a host compound such as α-, β- or γ-cyclodextrin.

The carbocyclic derivatives of this invention exist as optical isomers, due to the presence of asymmetric carbon atoms. The carbocyclic derivatives of the formula (I) also exist as geometrical isomers, due to the double bonds. The preferred isomers have the steric configuration of carbacyclin itself and are of the following formula (Ia):

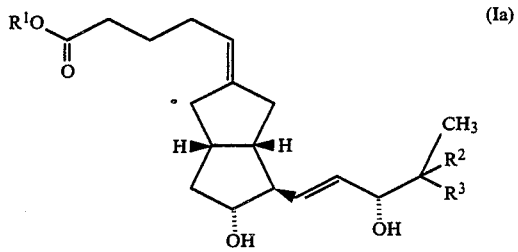

(wherein $R^1$, $R^2$ and $R^3$ as previously defined).

Examples of preferred carbocyclic derivatives of this invention are the compounds of formula (I), and their salts, where $R^1$, $R^2$ and $R^3$ are in accordance with the following table:

| number | $R^1$ | $R^2$ | $R^3$ |
|---|---|---|---|
| 1 | H | H | $CH_2CH_2CH=CH_2$ |
| 2 | $CH_3$ | H | $CH_2CH_2CH=CH_2$ |
| 3 | H | $CH_3$ | $CH_2CH_2CH=CH_2$ |
| 4 | $CH_3$ | $CH_3$ | $CH_2CH_2CH=CH_2$ |
| 5 | H | H | $CH_2CH_2CH_2CH=CH_2$ |
| 6 | $CH_3$ | H | $CH_2CH_2CH_2CH=CH_2$ |
| 7 | H | $CH_3$ | $CH_2CH_2CH_2CH=CH_2$ |
| 8 | $CH_3$ | $CH_3$ | $CH_2CH_2CH_2CH=CH_2$ |
| 9 | $C_6H_{13}$ | $CH_3$ | $CH_2CH_2CH_2CH=CH_2$ |
| 10 | $C_{10}H_{23}$ | $CH_3$ | $CH_2CH_2CH_2CH=CH_2$ |
| 11 | H | H | $CH_2CH_2CH_2CH=C(CH_3)_2$ |
| 12 | $CH_3$ | H | $CH_2CH_2CH_2CH=C(CH_3)_2$ |
| 13 | H | $CH_3$ | $CH_2CH_2CH_2CH=C(CH_3)_2$ |
| 14 | $CH_3$ | $CH_3$ | $CH_2CH_2CH_2CH=C(CH_3)_2$ |

Especially preferred carbocyclic derivatives of this invention are the numbers 3, 5, 7 and 8 listed above. The listed carbocyclic derivatives preferably take the form of the isomer which is in agreement with the general formula (Ia) given above.

Thus, the particularly preferred carbocyclic derivatives of this invention are:
16,16-dimethyl-19,20-didehydrocarbacyclin, and pharmaceutically acceptable salts thereof;
16-methyl-20-methylenecarbacyclin, and pharmaceutically acceptable salts thereof;
16,16-dimethyl-20-methylenecarbacyclin, and pharmaceutically acceptable salts thereof; and
16,16-dimethyl-20-methylenecarbacyclin methyl ester.

The carbocyclic derivatives of the present invention have low toxicity and typically possess a good anti-ulcer activity. The effectiveness of the compounds of this invention is concretely shown in comparison with existing prostacyclins.

EFFECT ON ASPIRIN-INDUCED ULCER

According to a method reported by Brodie and Chase [Gastroenterology 53, 604 (1967)], the anti-ulcer effect was determined. Five male rats of the Donryu strain (body weight 170 to 200 g) were used for each of the control and test compound groups. After being fasted for 24 hours, the rats were orally given certain concentrations of the test compounds and 15 minutes later given orally 100 mg/kg of aspirin (Sanko Pharmaceutical Inc). Four hours after the aspirin administration, the stomach was extracted and expanded with 10 ml of 0.5% formalin. An ulcer index was calculated from the total area of ulceration for the rats of the treated and control groups. The inhibition rate was calculated by comparing the ulcer indices of both groups.

The following table shows the inhibition rate (%) for each concentration of the test compounds from 10 γ/kg to 300 γ/kg (where γ is $10^{-6}$ g).

The reference compounds were as follows:
Reference Compound A: Carbacyclin
Reference Compound B: 17,18-Didehydrocarbacyclin
Reference Compound C: 20-Isopropylidenecarbacyclin
Reference Compound D: 17-Methyl-20-isopropylidenecarbacyclin

| | Inhibition Rate (%) | | | |
|---|---|---|---|---|
| | Concentration of the test compound, γ/kg | | | |
| Test Compound | 10 | 30 | 100 | 300 |
| Preparative Example 1 | 45 | 95 | 98 | — |
| Preparative Example 3 | — | 92 | — | — |
| Preparative Example 6 | — | 84 | — | — |
| Reference Compound A | — | — | 0 | 0 |
| Reference Compound B | — | 15 | 47 | — |
| Reference Compound C | — | — | — | 4 |
| Reference Compound D | — | 30 | 98 | — |

The results show that the carbocyclic derivatives of the present invention have, at a concentration of 30 γ/kg, an inhibition rate around 3 times higher than the rate of the other, reference compounds. It is apparent that the carbocyclic derivatives of the present invention have useful anti-ulcer activity.

TOXICITY TESTING

When the compound of Preparative Example 1 was intravenously administered to five rats at 10 mg per kg of body weight per rat, no deaths occurred. This favourable acute toxicity test indicates that the toxicity of the compounds of this invention is very low.

Thus, the compounds of the general formula (I) and pharmacologically acceptable salts thereof, representing compounds of the present invention, are of pharmaceutical use, especially for the therapeutic and preventive treatment of ulcers.

The present invention accordingly provides pharmaceutical compositions comprising a carbocyclic derivative of this invention, being a compound of the general formula (I) or a pharmaceutically acceptable salt thereof, together with a pharmaceutically acceptable carrier.

For the administration form, there may be mentioned oral administration by tablets, capsules, granules, powders and syrups, and forms for non-oral administration such as intravenous injection. The daily dose may vary depending on the symptoms, age and body weight. Usually from about 0.001 mg to about 1000 mg, preferably from about 0.01 mg to about 100 mg, is administered per day for an adult, once or by several divided doses.

The carbocyclic derivatives of this invention can be prepared by adaption of existing methods, for example by adaption of the method described in GB Patent Specification No. 2012265.

Thus, the compounds of the general formula (I) of this invention may be made by the steps shown in the following reaction scheme:

alkylenedithio group having from 1 to 4 carbon atoms, such as an ethylenedioxy or ethylenedithio group; or alkyloxy groups having from 1 to 4 carbon atoms such as dimethoxy or diethoxy groups.

The first step in the reaction scheme involves preparing an enone compound having the general formula (III). To this end, a formyl compound having the general formula (II) can be reacted with an anion having the general formula (VII):

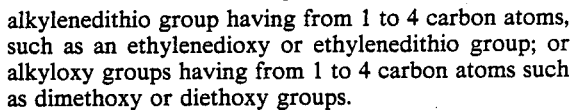

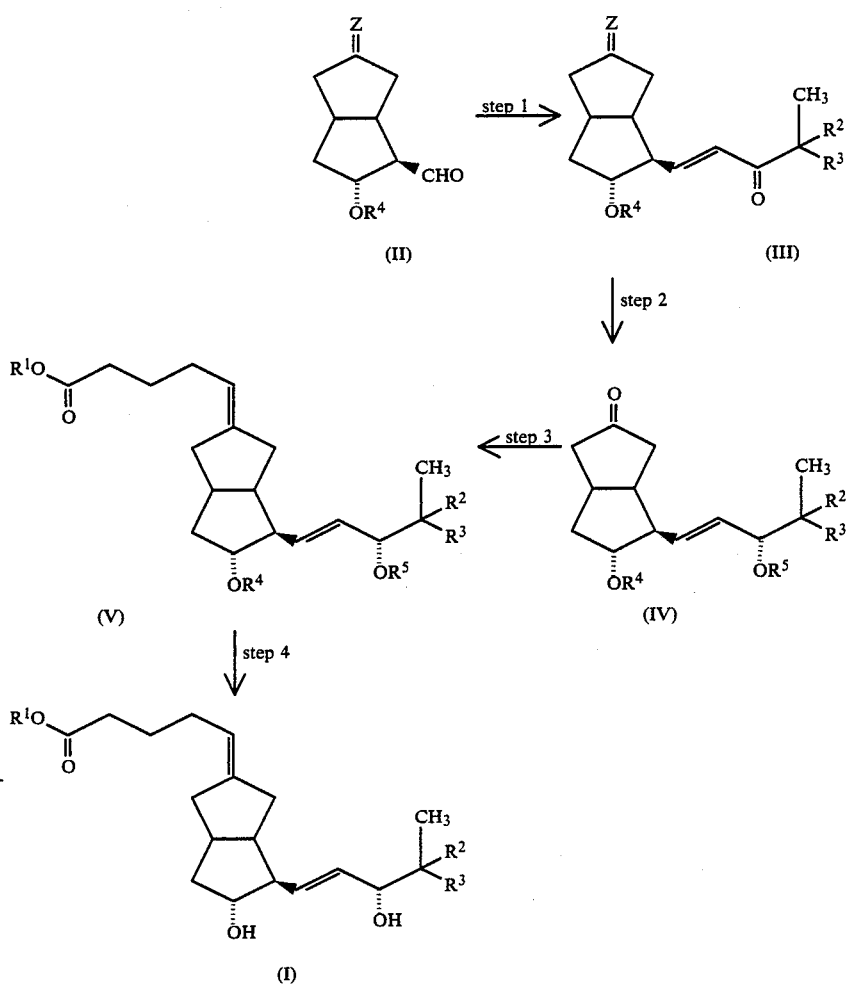

In this reaction scheme, $R^1$, $R^2$ and $R^3$ are as defined above, $R^4$ and $R^5$ are the same or different and each represents a hydroxy-protecting group, and Z represents a carbonyl-protecting group. Examples of hydroxy-protecting groups for $R^4$ and $R^5$ include, for instance, a heterocyclic group such as a tetrahydropyranyl or 4-methoxytetrahydropyran-4-yl group; a substituted methyl group such as a methoxymethyl or benzyloxymethyl group; or a silyl group such as a dimethyl-t-butylsilyl group. Examples of carbonyl-protecting groups for Z include, for instance, groups giving acetal formation, with Z either being a single divalent group or two monovalent groups. Thus, examples of carbonyl-protecting groups for Z include an alkylenedioxy or (wherein $R^2$ and $R^3$ are as defined above, $R^6$ represents an alkyl group of 1 to 4 carbon atoms, and M represents an alkali metal).

The anion of formula (VII) can easily be obtained from a compound of general formula (VI):

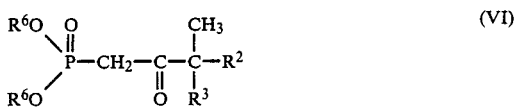

(where $R^2$, $R^3$ and $R^6$ are as defined above) by reaction with a base (for example, an alkali metal compound such as sodium hydride or n-butyllithium). The reaction with the base is typically effected at around room temperature for from 1 to 3 hours.

The second step in the reaction scheme involves preparing a ketone compound having the general formula (IV). This step can be achieved by reducing the unprotected carbonyl group of the compound (III) and removing the protecting group Z from the other, remaining carbonyl group. The reduction of the unprotected carbonyl group gives an alcohol, which is itself conveniently protected with the group $R^5$ after removal of the carbonyl-protecting group Z. If desired, the protecting group $R^4$ employed in the compound (III) can be removed as part of this second step, and then reprotection effected when introducing the protecting group $R^5$.

The reduction of the carbonyl group can be carried out, for example, by reacting the compound (III) with a reducing agent (for instance, a metal hydride compound such as sodium borohydride, sodium borocyanohydride or lithium trimethoxyaluminohydride) in an inert solvent (for example, an alcohol such as methanol) at from 0° to room temperature for from 30 minutes to 3 hours.

The conditions for removing the carbonyl-protecting group Z vary depending on the nature of the protecting group to be removed. If the protecting group is a dialkoxy or alkylenedioxy group, it can be removed by treating the compound with a mix of an acid and an aqueous solvent, such as acetic acid-water, dilute hydrochloric acid-aqueous acetone, dilute hydrochloric acid-aqueous acetonitrile, dilute sulfuric acid-aqueous acetone or boron trifluoride etherate-aqueous acetone. If the protecting group is an alkylenedithio group, it can be removed by treating the compound with a suitable mercury reagent, such as mercuric chloride or mercuric oxide, in an inert solvent (for example, an ether such as dioxane, tetrahydofuran or diethyl ether). The removal of the group Z is conveniently carried out at around room temperaure for from 1 to 15 hours.

The conditions for introducing the hydroxy-protecting group $R^5$ will also vary depending on the nature of the protecting group. If the desired protecting group is a heterocyclic group, reaction can be carried out by treatment with a heterocyclic compound, such as dihydropyran or 4-methoxydihydropyran, in the presence of an acid (for example, hydrochloric acid, trifluoroacetic acid or p-toluenesulfonic acid) typically at from 0° C. to room temperature for from 1 to 3 hours in an inert solvent (for example, a halogenated hydrocarbon such as methylene chloride). If the desired protecting group is a silyl group, reaction can be carried out by treatment with a corresponding halide in the presence of an organic amine (for example, pyridine, imidazole or triethylamine) typically around room temperature for from 1 to 3 hours in an inert solvent (for example, an aromatic hydrocarbon such as benzene).

The third step in the reaction scheme involves preparing a carbacyclin compound having the general formula (V). It can be carried out by treating the compound (IV) with a Wittig reagent of the general formula (VIII):

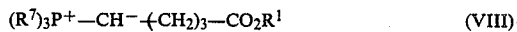

(where $R^1$ is as defined above and $R^7$ represents an alkyl group having from 1 to 4 carbon atoms or an aryl group such as a phenyl group). The reaction with the Wittig reagent is suitably effected in an inert solvent (for example, an ether such as tetrahydrofuran, an aromatic hydrocarbon such as toluene, or a sulfoxide such as dimethyl sulfoxide), preferably in a stream of an inert gas such as nitrogen or argon.

The Wittig reagent of general formula (VIII) can itself be prepared by treating a compound of the general formula (IX):

(where $R^1$ and $R^7$ are as defined above, and X represents a hydrogen atom such as chlorine or bromine) with a base, for example, an alkali metal hydride such as sodium hydride, an alkali metal alkoxide such as sodium ethoxide or potassium t-butoxide, or an alkali metal dimethylsulfoxide anion such as sodium dimethylsulfoxide ("dimsyl") anion, typically around room temperature for from 1 to 24 hours.

The fourth step in the reaction scheme involves preparing a desired carbacyclin compound having the general formula (I). This step can be achieved by removing the hydroxy-protecting groups $R^4$ and $R^5$ from the compound (V).

The conditions for the removal depend on the nature of the protecting group to be removed. If the protecting group is a heterocyclic or substituted methyl group, removal can be achieved by treatment with an acid (for example, an organic acid such as acetic acid, trifluoroacetic acid, p-toluenesulfonic acid, or camphorsulfonic acid; or a mineral acid such as hydrochloric acid or sulfuric acid) in an inert solvent (for example, aqueous acetone or aqueous tetrahydrofuran) typically at from room temperature to 100° C. for from 30 minutes to 5 hours. If the protecting group is a silyl group, removal can be carried out in water by treatment with an acid (for example, an organic acid such as acetic acid or trifluoroacetic acid; or a mineral acid such as hydrochloric acid or sulfuric acid), with a base (for example, an alkali such as sodium hydroxide or potassium carbonate) or with tetrabutylammonium fluoride, typically around room temperature for from 30 minutes to 3 hours. A silyl group can be also removed by treatment with an ammonium salt such as tetra-n-butylammonium fluoride in an inert solvent (for example, ether).

A compound of general formula (I) wherein $R^1$ is a hydrogen atom may then readily be converted to give a pharmacologically acceptable salt, for example by conventional salification.

A compound of the general formula (I) in which $R^1$ is a hydrogen atom can be converted into a compound (I) in which $R^1$ is an alkyl group by conventional means. Esterification may be performed for example with a diazoalkane such as diazomethane, diazoethane or diazopropane, or with an alcohol-mineral acid such as methanol-hydrochloric acid, ethanol-hydrochloric acid or n-pentanol-hydrochloric acid.

Correspondingly, a compound (I) in which $R^1$ is an alkyl group can be converted into a compound (I) in which $R^1$ is a hydrogen atom by conventional means. Hydrolysis may be performed, for example, by reaction with an alkali metal hydroxide in an aqueous solvent, such as sodium hydroxide-aqueous methanol.

A compound in which $R^1$ is an alkyl group can if desired be converted into a compound in which $R^1$ is another alkyl group by conventional means. Ester exchange may be performed, for example, by reaction with an alcohol in the presence of a base such as potassium carbonate.

At the completion of each step in the reaction scheme the respective product can be isolated from the reaction mixture by conventional means. For example, after completion of a reaction step, the reaction mixture may, if appropriate, be neutralized or acidified, then extracted with a suitable organic solvent. Such an extract can be washed, dried and the product obtained by distilling off the solvent. The product at each step can if necessary be purified by conventional means such as column chromatography, thin layer chromatography and/or recrystallization. Where the product is obtained as a mixture of geometric and/or optical isomers, the isomers can be separated and resolved at any suitable step of the reaction scheme.

The present invention is illustrated by the following non-limiting examples.

PREPARATIVE EXAMPLE 1

16-Methyl-20-methylenecarbacyclin (a) 2β-(3-Oxo-4-methylnona-1,8-dienyl)-3α-(2-tetrahydropyranyloxh)-7,7-ethylenedioxy-cis-bicyclo[3.3.0]octane 482 mg of sodium hydride (a 55% dispersion in mineral oil) was washed with hexane and mixed with 100 ml of anhydrous tetrahydrofuran. The resultant suspension was cooled on an ice bath, 3.12 g of dimethyl 2-oxo-3-methyl-7-octenylphosphonate was added, and the mixture stirred for 40 minutes. The solution was ice-cooled and 2.69 g of 2β-formyl-3α-(2-tetrahydropyranyloxy)-7,7-ethylenedioxy-cis-bicyclo[3.3.0]octane dissolved in 15 ml of tetrahydrofuran was mixed therewith and stirred for 2 hours. After completion of the reaction, 100 ml of saturated aqueous sodium chloride solution was added and the mixture extracted with ethyl acetate. The extracted solution was washed with saturated aqueous sodium chloride solution and dried over anhydrous sodium sulfate. Evaporation of the solvent gave 4.57 g of residue which was purified by column chromatography using 90 g of alumina. The fraction eluted with hexane containing from 1 to 9% ethyl acetate gave 3.08 g of the desired compound as an oil.

infrared absorption spectrum (liq) $v_{max}$cm$^{-1}$: 1020, 1120, 1626, 1668, 1692 nuclear magnetic resonance spectrum (CDCl$_3$) δppm: 1.07 (3H, doublet); 3.89 (4H, singlet); 4.8-6.0 (3H, multiplet); 6.0-7.1 (2H, multiplet).

(b) 2β-(3-Hydroxy-4-methylnona-1,8-dienyl)-3α-(2-tetrahydropyranyloxy)-7,7-ethylenedioxy-cis-bicyclo[3.3.0octane To 3.26 g of cerium chloride heptahydrate dissolved in 25 ml of methanol was added 3.05 g of the enone compound prepared in Preparative Example 1(a) dissolved in 23 ml of methanol at from 0° to 5° C. 470 mg of sodium borohydride at from 0° to 3° C. was then added to the reaction solution with stirring, and the mixture stirred for 30 minutes at the same temperature. After completion of the reaction, water was added and the system extracted with ethyl acetate. The extracted solution was washed with a saturated aqueous solution of sodium chloride and dried over anhydrous sodium sulfate. After distilling off the solvent, 3.01 g of the desired compound was obtained as an oil.

infrared absorption spectrum (liq) $v_{max}$ cm$^{-1}$: 1020, 1120, 1640, 3475 nuclear magnetic resonance spectrum (CDCl$_3$) δppm: 0.89 (3H, multiplet); 3.88 (4H, singlet); 4.67 (1H, broad singlet); 4.8-6.3 (5H, multiplet).

(c) 2β-(3α-Hydroxy-4-methylnona-1,8-dienyl)-3α-hydroxy-7-oxo-cis-bicyclo[3.3.0]octane and 2β-(3β-hydroxy-4-methylnona-1,8-dienyl)-3α-hydroxy-7-oxo-cis-bicyclo[3.3.0]octane 2.97 g of the hydroxy compound prepared in Preparative Example 1(b) was dissolved in 6 ml of tetrahydrofuran, and to the solution was added 6.1 ml of acetic acid and 11 ml of water. The resultant mixture was then stirred at from 45° to 50° C. for 2.5 hours. During this stirring, 20 ml of water divided into 8 aliquots were added. After cooling of the reaction solution, 20% aqueous sodium chloride solution was added to give neutrality, further saturated aqueous sodium chloride solution was added, and the system extracted with ethyl acetate. The organic layer was washed with saturated aqueous sodium chloride solution and dried over anhydrous sodium sulfate. Evaporation of the solvent gave 2.61 g of residue which was purified by column chromatography using 78 g of silica gel. The fraction eluted with hexane containing from 38 to 44% ethyl acetate gave 591 mg of the 2β-(3β-hydroxy) compound as an oil, the fraction eluted with hexane containing from 44 to 54% ethyl acetate gave 279 mg of a mixture of the 2β-(3α-hydroxy) and 2β-(3β-hydroxy) compounds, and the fraction eluted with hexane containing from 54 to 95% ethyl acetate gave 937 mg of the 2β-(3α-hydroxy) compound as an oil.

2β-(3α-hydroxy) compound:

infrared absorption spectrum (liq) $v_{max}$ cm$^{-1}$: 1640, 1738, 3400.

nuclear magnetic resonance spectrum (CDCl$_3$) δppm: 0.86 (3H, multiplet); 3.95 (2H, broad), 4.80-6.20 (5H, multiplet).

2β-(3β-hydroxy) compound infrared absorption spectrum (liq) $v_{max}$ cm$^-$: 1640, 1730, 3400.

nuclear magnetic resonance spectrum (CDCl$_3$) δppm: 0.90 (3H, doublet); 3.95 (2H, broad), 4.8-6.2 (5H, multiplet).

(d) 2β-[3α-(2-Tetrahydropyranyloxy)-4-methylnona-1,8-dienyl)]-3α-(2-tetrahydropyranyloxy)-7-oxo-cis-bicyclo[3.3.0octane 900 mg of the 2β-(3α-hydroxy) compound prepared in Preparative Example 1(c) was dissolved in 15 ml of methylene chloride. The solution was added to 0.85 ml of dihydropyran. While cooling the solution with ice, 10 mg of p-toluenesulfonic acid was added and the mixture stirred for 100 minutes. Saturated sodium bicarbonate solution was added, then saturated aqueous sodium chloride solution, and the styrene extracted with ethyl acetate. The organic layer was washed with saturated aqueous sodium chloride solution and dried over anhydrous sodium sulfate. After distilling off the solvent, 1.49 g of the crude desired compound was obtained as an oil.

infrared absorption spectrum (liq) $v_{max}$ cm$^{-1}$: 1020, 1030, 1130, 1640, 1740.

nuclear magnetic resonance spectrum (CDCl$_3$) δppm: 0.86 (3H, multiplet); 4.70 (2H, broad singlet); 5.9-6.2 (5H, multiplet).

(e) 16-Methyl-20-methylenecarbacyclin 11,15-ditetrahydropyranyl ether and its 5Z-isomer.

Dimsyl sodium which had been previously prepared from 1.25 g of sodium hydride (55% dispersion in mineral oil) and 80 ml of dimethyl sulfoxide, was dissolved in dimethyl sulfoxide. Under a stream of nitrogen, 8.65 g of triphenyl 4-carboxybutylphosphonium bromide was added. After stirring for 20 minutes, 25 ml of dimethyl sulfoxide containing 1.46 g of the ketone compound prepared in Preparative Example 1(d) was added and the mixture allowed to stand overnight. After completion of the reaction, 30 ml of ice water, 50 ml of cyclohexane and 1.0 ml of concentrated hydrochloric acid were added in this order and the layers were separated. The aqueous layer was extracted with cyclohexane, and the combined organic layers were washed with saturated aqueous sodium chloride solution, and then dried anhydrous sodium sulfate. After distilling off the solvent, 2.62 g of the resulting residue was purified by column chromatography using 40 g of silica gel. The fraction eluted with hexane containing from 13 to 15% ethyl acetate gave 345 mg of the 5Z-isomer, then the fraction eluted with hexane containing from 15 to 19% ethyl acetate gave 107 mg of a mixture of the 5Z-isomer and the 5E-isomer and finally the fraction eluted with hexane containing from 20 to 55% ethyl acetate gave 804 mg of the 5E-isomer as an oil.

5Z-Isomer infrared absorption spectrum (liq) $v_{max}$ cm$^{-1}$: 973, 1640, 1708, 1740.

nuclear magnetic resonance spectrum (CDCl$_3$) $\delta$ppm: 0.90 (3H, multiplet); 4.60–6.20 (8H, multiplet).

5E-Isomer infrared absorption spectrum (liq) $v_{max}$ cm$^{-1}$: 974, 1020, 1640, 1708, 1736.

nuclear magnetic resonance spectrum (CDCl$_3$) $\delta$ppm: 0.90 (3H, multiplet); 4.60–6.20 (8H, multiplet).

(f) 16-Methyl-20-methylenecarbacyclin

To 23 ml of acetone containing 750 mg of the 5E-isomer of the dipyranyl compound prepared in Preparative Example 1(e) was added 10 ml of water and 40 mg of camphorsulfonic acid. The resultant was heated and stirred at about 60° C. for 90 minutes. After completion of the reaction, 25 ml of water was added and the system extracted with ethyl acetate. The extracted solution was washed with water and dried over anhydrous sodium sulfate. After distilling off the solvent, the resulting residue was purified by column chromatography using 13 g of silica gel. The fractions eluted with hexane containing 40% ethyl acetate and succeedingly with ethyl acetate gave 338 mg of the desired compound as an oil.

infrared absorption spectrum (liq) $v_{max}$ cm$^{-1}$: 1640, 1708, 3340.

nuclear magnetic resonance spectrum (CDCl$_3$) $\delta$ppm: 0.86 (3H, multiplet); 3.3–4.1 (2H, broad); 4.8–6.2 (6H, multiplet).

A corresponding methyl ester was obtained by esterification of this compound with diazomethane.

infrared absorption spectrum (liq) $v_{max}$ cm$^{-1}$: 970, 1640, 1735, 3370.

PREPARATIVE EXAMPLE 2

16-Methyl-19,20-didehydrocarbacyclin (a) 2$\beta$-(3-Oxo-4-methylocta-1,7-dienyl)-3$\alpha$-(2-tetrahydropyranyloxy)-7,7-ethylenedioxy-cis-bicyclo[3.3.0]octane From 439 mg of sodium hydride (55% dispersion in mineral oil), 2.95 g of dimethyl 2-oxo-3-methyl-6-octenylphosphonate and 2.60 g of 2$\beta$-formyl-3$\alpha$-(2-tetrahydropyranyloxy)-7,7-ethylenedioxy-cis-bicyclo[3.3.0]octane, 3.23 g of the desired compound was obtained as an oil by similar reaction and treatment to Preparative Example 1(a).

infrared absorption spectrum (liq) $v_{max}$ cm$^{-1}$: 1030, 1120, 1622, 1668, 1694.

nuclear magnetic resonance spectrum (CDCl$_3$) $\delta$ppm: 1.10 (3H, doublet); 3.92 (4H, singlet); 4.68 (1H, multiplet); 4.8–7.2 (5H, multiplet).

(b) 2$\beta$-(3-Hydroxy-4-methylocta-1,7-dienyl)-3$\alpha$-(2-tetrahydropyranyloxy)-7,7-ethylenedioxy-cis-bicyclo[3.3.0]octane From 3.53 g of cerium chloride heptahydrate, 507 mg of sodium borohydride and 3.19 g of the enone compound prepared in Preparative Example 2(a), 3.15 g of the desired compound could be obtained as an oil by similar reaction and treatment to Preparative Example 1(b).

infrared absorption spectrum (liq) $v_{max}$ cm$^{-1}$: 1020, 1120, 1640, 3480.

nuclear magnetic resonance spectrum (CDCl$_3$) $\delta$ppm: 0.90 (3H, multiplet); 4.70 (1H, broad); 4.80–6.2 (5H, multiplet).

(c) 2$\beta$-(3$\alpha$-Hydroxy-4-methylocta-1,7-dienyl)-3$\alpha$-hydroxy-7-oxo-cis-bicyclo[3.3.0]octane and 2$\beta$-(3$\beta$-hydroxy-4-methylocta-1,7-dienyl)-3$\alpha$-hydroxy-7-oxo-cis-bicyclo[3.3.0]octane From 3.12 g of the hydroxy compound prepared in Preparative Example 2(b) and 6.6 ml of acetic acid, 970 mg of oily 2$\beta$-(3$\alpha$-hydroxy) compound and 535 mg of oily 2$\beta$-(3$\beta$-hydroxy) compound was obtained by similar reaction and treatment to Preparative Example 1(c).

2$\beta$-(3$\alpha$-hydroxy) compound infrared absorption spectrum (liq) $v_{max}$ cm$^{-1}$: 1640, 1738, 3400.

nuclear magnetic resonance spectrum (CDCl$_3$) $\delta$ppm: 0.89 (3H, multiplet); 4.8–6.2 (5H, multiplet).

2$\beta$-(3$\beta$-hydroxy) compound infrared absorption spectrum (liq) $v_{max}$ cm$^{-1}$: 1640, 1730, 3400.

nuclear magnetic resonance spectrum (CDCl$_3$) $\delta$ppm: 0.88 (3H, doublet); 4.8–6.2 (5H, multiplet).

(d) 2$\beta$-[3$\alpha$-(2-Tetrahydropyranyloxy)-4-methylocta-1,7-dienyl]-3$\alpha$-(2-tetrahydropyranyloxy)-7-oxo-cis-bicyclo[3.3.0]octane From 900 mg of the 2$\beta$-(3$\alpha$-hydroxy) compound prepared in Preparative Example 2(c) and 0.89 ml of dihydropyran, 1.51 g of the crude desired compound was obtained as an oil by similar reaction and treatment to Preparative Example 1(d).

infrared absorption spectrum (liq) $v_{max}$ cm$^{-1}$: 970, 1020, 1032, 1130, 1640, 1740.

nuclear magnetic resonance spectrum (CDCl$_3$) $\delta$ppm: 0.90 (3H, multiplet); 4.5–6.2 (7H, multiplet).

(e) 16-Methyl-19,20-didehydrocarbacyclin-11,15-ditetrahydropyranyl ether

From 1.39 g of sodium hydride (55% dispersion in mineral oil), 64 ml of dimethyl sulfoxide, 9.35 g of triphenyl-4-carboxybutylphosphonium bromide and 1.58 g of the ketone compound prepared in Preparative Example 2(d), 695 mg of the desired compound as an oil and 370 mg of its 5Z-isomer were obtained by similar reaction and treatment to Preparative Example 1(e).

5E-Isomer infrared absorption spectrum (liq) $v_{max}$ cm$^{-1}$: 1020, 1640, 1708, 1738.

nuclear magnetic resonance spectrum (CDCl$_3$) $\delta$ppm: 0.90 (3H, multiplet); 4.5–6.2 (8H, multiplet).

5Z-Isomer infrared absorption spectrum (liq) $v_{max}$ cm$^{-1}$: 1020, 1640, 1710, 1740.

(f) 16-Methyl-19,20-didehydrocarbacyclin

From 665 mg of the dipyranyl 5E-isomer prepared in Preparative Example 2(e), 345 mg of the desired compound was obtained as an oil by similar reaction and treatment to Preparative Example 1(f).

infrared absorption spectrum (liq) $v_{max}$ cm$^{-1}$: 970, 1640, 1708, 3350.

nuclear magnetic resonance spectrum (CDCl$_3$) δppm: 0.88 (3H, multiplet); 3.3–4.1 (2H, broad); 4.8–62. (6H, multiplet).

PREPARATIVE EXAMPLE 3

16,16-Dimethyl-20-methylenecarbacyclin (a) 2β-(3-Oxo-4,4-dimethylnona-1,8-dienyl)-3α-(2-tetrahydropyranyloxy)-7,7-ethylenedioxy-cis-bicyclo[3.3.0]octane From 440 mg of sodium hydride (55% dispersion in mineral oil), 3.30 g of dimethyl 2-oxo-3,3-dimethyl-7-octenyl phosphonate and 2.50 g of 2β-formyl-3α-(2-tetrahydropyranyloxy)-7,7-ethylenedioxy-cis-bicyclo[3.3.0]octane, 3.09 g of the desired compound was obtained as an oil by similar reaction and treatment to Preparative Example 1(a).

infrared absorption spectrum (liq) $v_{max}$ cm$^{-1}$: 985, 1030, 1625, 1691.

nuclear magnetic resonance spectrum (CDCl$_3$) δppm: 1.12 (6H, singlet); 3.90 (4H, singlet); 4.5–4.8 (1H, multiplet); 4.8–6.1 (3H, multiplet); 6.4–7.1 (2H, multiplet).

(b) 2β-(3-Hydroxy-4,4-dimethylnona-1,8-dienyl)-3α-(2-tetrahydropyranyloxy)-7,7-ethylenedioxy-cis-bicyclo[3.3.0]octane From 2.66 g of cerium chloride heptahydrate, 350 mg of sodium borohydride and 3.07 g of the enone compound prepared in Preparative Example 3(a), 3.03 g of the desired compound was obtained as an oil by similar reaction and treatment to Preparative Example 1(b).

infrared absorption spectrum (liq) $v_{max}$ cm$^{-1}$: 975, 1022, 1641, 3490.

nuclear magnetic resonance spectrum (CDCl$_3$) δppm: 0.85 (3H, singlet); 0.89 (3H, singlet); 3.91 (4H, singlet); 4.70 (1H, broad), 4.8–6.1 (5H, multiplet).

(c) 2β-(3α-Hydroxy-4,4-dimethylnona-1,8-dienyl)-3α-hydroxy-7-oxo-cis-bicyclo[3.3.0]octane and 2β-(3β-hydroxy-4,4-dimethylnona-1,7-dienyl)-3α-hydroxy-7-oxo-cis-bicyclo[3.3.0]octane From 3.03 g of the hydroxy-compound prepared in Preparative Example 3(b) and 30 ml of acetic acid, 1.31 g of oily 2β-(3α-hydroxy) compound and 760 mg of oily 2β-(3β-hydroxy) compound were obtained by similar reaction and treatment to Preparative Example 1(c).

2β-(3α-hydroxy) compound infrared absorption spectrum (liq) $v_{max}$ cm$^{-1}$: 975, 1642, 1740, 3420.

nuclear magnetic resonance spectrum (CDCl$_3$) δppm: 0.85 (3H, singlet); 0.89 (3H, singlet); 3.7–4.1 (2H, multiplet); 4.8–6.2 (5H, multiplet).

2β-(3β-hydroxy) compound infrared absorption spectrum (liq) $v_{max}$ cm$^{-1}$: 974, 1641, 1740, 3420.

(d) 2β-[3α-(2-Tetrahydropyranyloxy)-4,4-dimethylnona-1,8-dienyl]-3α-(2-tetrahydropyranyloxy)-7-oxo-cis-bicyclo[3.3.0]octane From 1.29 g of the 2β-(3α-hydroxy) compound prepared in Preparative Example 3(c) and 1.15 ml of dihydropyran, 1.98 g of the crude desired compound was obtained as an oil by similar reaction and treatment to Preparative Example 1(d).

infrared absorption spectrum (liq) $v_{max}$ cm$^{-1}$: 1022, 1034, 1642, 1742.

nuclear magnetic resonance spectrum (CDCl$_3$) δppm: 0.7–1.0 (6H, multiplet); 4.68 (2H, broad), 4.8–6.2 (5H, multiplet).

(e) 16,16-Dimethyl-20-methylenecarbacyclin-11,15-ditetrahydropyranyl ether

From 1.63 g of sodium hydride (55% dispersion in mineral oil), 100 ml of dimethyl sulfoxide, 10.12 g of triphenyl 4-carboxybutylphosphonium bromide and 1.97 g of the ketone compound prepared in Preparative Example 3(d); 1.06 g of the desired compound as an oil and 0.6 g of its 5Z-isomer were obtained by similar reaction and treatment to Preparative Example 1(e).

5E-Isomer infrared absorption spectrum (liq) $v_{max}$ cm$^{-1}$: 980, 1645, 1714, 1741.

nuclear magnetic resonance spectrum (CDCl$_3$) δppm: 0.7–1.0 (6H, multiplet); 4.6–6.2 (8H, multiplet).

5Z-Isomer infrared absorption spectrum (liq) $v_{max}$ cm$^{-1}$: 980, 1645, 1714, 1741.

(f) 16,16-Dimethyl-20-methylenecarbacyclin

In 21 ml of acetic acid, 1.05 g of the 5E-isomer of the dipyranyl compound prepared in Preparative Example 3(e) was dissolved. To this solution was added 5 ml of water, and the mixture stirred at room temperature. After 0.5 and again after 1 hour, 2.5 ml of water was added and the reaction solution was stirred for a further 14 hours. After completion of the reaction, 50 ml of 20% sodium hydroxide solution was added, followed by saturated sodium chloride solution, and the system extracted with ethyl acetate. The extracted solution was washed with saturated solution of sodium chloride and dried over anhydrous sodium sulfate. After distilling off the solvent, the resulting residue was purified by silica gel column chromatography to give 0.56 g of the desired compound as an oil.

infrared absorption spectrum (liq) $v_{max}$ cm$^{-1}$: 970, 1640, 1710, 3380.

nuclear magnetic resonance spectrum (CDCl$_3$) δppm: 0.86 (3H, singlet); 0.90 (3H, singlet); 3.4–4.0 (2H, multiplet); 4.8–6.2 (6H, multiplet).

The product compound was esterified with diazomethane to afford the corresponding methyl ester.

infrared absorption spectrum (liq) $v_{max}$ cm$^{-1}$: 973, 1438, 1642, 1742, 3400.

PREPARATIVE EXAMPLE 4

16,16-Dimethyl-19,20-didehydrocarbacyclin (a) 2β-(3-Oxo-4-methylocta-1,7-dienyl)-3α-(2-tetrahydropyranyloxy)-7,7-ethylenedioxy-cis-bicyclo[3.3.0]octane From 430 mg of sodium hydride (55% dispersion in mineral oil), 2.90 g of dimethyl 2-oxo-3,3-dimethyl-6-heptenylphosphonate and 2.60 g of 2β-formyl-3α-(2-tetrahydropyranyloxy)-7,7-ethylenedioxy-cis-bicyclo[3.3.0]octane, 3.20 g of the desired compound was obtained as an oil by similar reaction and treatment to Preparative Example 1(a).

infrared absorption spectrum (liq) $v_{max}$ cm$^{-1}$: 985, 1030, 1625, 1690.

nuclear magnetic resonance spectrum (CDCl$_3$) δppm: 1.12 (6H, singlet); 3.94 (4H, singlet); 4.5–4.8 (1H, multiplet); 4.8–6.1 (3H, multiplet); 6.4–7.1 (2H, multiplet).

(b) 2β-(3-Hydroxy-4,4-dimethylocta-1,7-dienyl)-3α-(2-tetrahydropyranyloxy)-7,7-ethylenedioxy-cis-bicyclo[3.3.0]octane From 3.52 g of cerium chloride heptahydrate, 508 mg of sodium borohydride and 3.09 g of the enone compound prepared in Preparative Example 4(a), 3.05 g of the desired compound was obtained as an oil by similar reaction and treatment to Preparative Example 1(b).

infrared absorption spectrum (liq) $v_{max}$ cm$^{-1}$: 974, 1020, 1641, 3490.

nuclear magnetic resonance spectrum (CDCl$_3$) δppm: 0.84 (3H, singlet); 0.89 (3H, singlet); 3.91 (4H, singlet); 4.70 (1H, broad); 4.1–4.8 (5H, multiplet).

(c) 2β-(3α-Hydroxy-4,4-dimethylocta-1,7-dienyl)-3α-hydroxy-7-oxo-cis-bicyclo[3.3.0]octane and 2β-(3β-hydroxy-4,4-dimethylocta-1,7-dienyl)-3α-hydroxy-7-oxo-cis-bicyclo[3.3.0]octane From 3.02 g of the hydroxy compound prepared in Preparative Example 4(b) and 6.6 ml of acetic acid, 1.33 g of 2β-(3α-hydroxy) compound and 759 mg of 2β-(3β-hydroxy) compound were obtained, both as oils, by similar reaction and treatment to Preparative Example 1(c).

2β-(3α-hydroxy) compound
infrared absorption spectrum (liq) $v_{max}$ cm$^{-1}$: 975, 1641, 1740, 3421.

nuclear magnetic resonance spectrum (CDCl$_3$) δppm: 0.84 (3H, singlet); 0.89 (3H, singlet); 3.7–4.1 (2H, multiplet); 4.8–6.2 (5H, multiplet).

2β-(3β-hydroxy) compound
infrared absorption spectrum (liq) $v_{max}$ cm$^{-1}$: 974, 1641, 1740, 3420.

(d) 2β-[3α-(2-Tetrahydropyranyloxy)-4,4-dimethylocta-1,7-dienyl]-3α-(2-tetrahydropyranyloxy)-7-oxo-cis-bicyclo[3.3.0]octane From 880 mg of the 2β-(3α-hydroxy) compound prepared in Preparative Example 4(c) and 0.86 ml of dihydropyran, 1.32 g of the crude desired compound was obtained as an oil by similar reaction and treatment to Preparative Example 1(d).

infrared absorption spectrum (liq) $v_{max}$ cm$^{-1}$: 1022, 1034, 1642, 1741.

nuclear magnetic resonance spectrum (CDCl$_3$) δppm: 0.7–1.0 (6H, multiplet); 4.67 (2H, broad.), 4.8–6.2 (5H, multiplet).

(e) 16,16-Dimethyl-19,20-didehydrocarbacyclin-11,15-ditetrahydropyranyl ether

From 1.39 g of sodium hydride (55% dispersion in mineral oil), 60 ml of dimethyl sulfoxide, 9.39 g of triphenyl-4-carboxybutylphosphonium bromide and 1.31 g of the ketone compound prepared in Preparative Example 4(d), 659 mg of the desired compound as an oil and 341 mg of its 5Z-isomer were obtained by similar reaction and treatment to Preparative Example 1(e).

5E-Isomer
infrared absorption spectrum (liq) $v_{max}$ cm$^{-1}$: 980, 1644, 1713, 1741.

nuclear magnetic resonance spectrum (CDCl$_3$) δppm: 0.7–1.0 (6H, multiplet); 4.6–6.2 (8H, multiplet).

5Z-Isomer
infrared absorption spectrum (liq) $v_{max}$ cm$^{-1}$: 980, 1644, 1713, 1741.

(f) 16,16-Dimethyl-19,20-didehydrocarbacyclin

From 630 mg of the 5E-isomer of the dipyranyl compound prepared in Preparative Example 4(e), 314 mg of the desired compound was obtained as an oil by similar reaction and treatment to preparative Example 3(f).

infrared absorption spectrum (liq) $v_{max}$ cm$^{-1}$: 972, 1640, 1710, 3380.

nuclear magnetic resonance spectrum (CDCl$_3$) δppm: 0.86 (3H, singlet); 0.90 (3H, singlet); 3.4–4.0 (2H, multiplet); 4.8–6.2 (6H, multiplet).

PREPARATIVE EXAMPLE 5

16-Methyl-20-methylenecarbacyclin decyl ester 200 mg of the methyl ester compound prepared in Preparative Example 1(f) was dissolved in 2 ml of decyl alcohol. 100 mg of potassium carbonate was added and the mixture stirred for 2 hours at 100° C. After cooling of the reaction solution, sodium chloride solution was added, and the system extracted with ethyl acetate. The extracted solution was washed with sodium chloride solution and dried over anhydrous sodium sulfate. After distilling off the solvent, the residue was purified by silica gel column chromatography. The fraction eluted with hexane containing from 30 to 50% ethyl acetate gave 209 mg of the desired compound as an oil.

infrared absorption spectrum (liq) $v_{max}$ cm$^{-1}$: 965, 1170, 1378, 1450, 1640, 1735.

PREPARATIVE EXAMPLE 6

16-Methyl-20-isopropylidenecarbacyclin (a) 2β-(3-Oxo-4,9-dimethyldeca-1,8-dienyl)-3α-(2-tetrahydropyranyloxy)-7,7-ethylenedioxy-cis-bicyclo[3.3.0]octane.

The same procedures as in the above preparative example 1(a) were followed, except that there was employed 483 mg of sodium hydride (55% dispersion in mineral oil), 3.48 g of dimethyl 2-oxo-3,8-dimethyl-7-nonenylphosphonate and 2.69 of 2β-formyl-3α-(2-tetrahydropynanyloxy)-7,7-ethylene-dioxy-cis-bicyclo[3.3.0]octane, there was obtained 3.36 g of the desired product as an oily substance.

infrared absorption spectrum (liq) $v_{max}$ cm$^{-1}$: 1030, 1120, 1622, 1665, 1692.

nuclear magnetic resonance spectrum (CDCl$_3$) δppm: 1.10 (3H, singlet); 1.58 (3H, singlet); 1.67 (3H, singlet); 4.68 (1H, multiplet); 4.87 (4H, singlet); 5.10 (1H, multiplet); 6.0–6.9 (2H, multiplet).

(b) 2β-(3-Hydroxy-4,9-dimethyldeca-1,8-dienyl)-3α-2-tetrahydropyranyloxy)-7,7-ethylenedioxy-cis-biycyclo[3.3.0]octane The same procedures were followed as in the above Preparative Example 1(b), except that there was employed 3.35 g of cerium chloride heptahydrate, 485 mg of sodium borohydride and 3.34 g of the enone prepared in Preparative Example 6(a), there was obtained 3.34 g of the desired product as an oily substance.

infrared absorption spectrum (liq) $v_{max}$ cm$^{-1}$: 1020, 1120, 3475.

nuclear magnetic resonance spectrum (CDCl$_3$) δppm: 0.90 (3H, multiplet); 3.88 (1H, broad); 4.67 (1H, broad); 5.15 (1H, multiplet); 5.58 (2H, multiplet).

(c) 2β-(3α-hydroxy-4,9-dimethyldeca-1,8-dienyl)-3α-hydroxy-7-oxo-cis-bicyclo[3.3.0]octane Following the same procedure as in the above Preparative Example 1(c) except for the use of 3.29 g of the hydroxy compound prepared in Preparative Example 6(b) and 8.3 ml of acetic acid, there was obtained 950 mg of the desired product as an oil substance.

infrared absorption spectrum $v_{max}$ cm$^{-1}$: 1738, 3400.

nuclear magnetic resonance spectrum (CDCl$_3$) δppm: 0.93 (3H, multiplet); 1.60 (3H, singlet); 1.68 (3H, singlet); 5.12 (1H, multiplet); 5.46 (2H, multiplet).

(d) 2β-[3α-(2-Tetrahydropyranyloxy)-4,9-dimethyl-deca-1,8-dienyl]-3α-(2-tetrahydropyranyloxy)-7-oxo-cis-bicyclo[3.3.0]octane Following the same procedure as in the above Preparative Example 1(d) except for use of 910 mg of the 2β-(3α-hydroxy) compound prepared in Preparative Example 6(c) and 0.8 ml of dihydropyran, there were obtained 1.50 g of the crude desired product as an oily substance.

infrared absorption spectrum (liq) $v_{max}$ cm$^{-1}$: 966, 1018, 1032, 1740.

(e) 16-Methyl-20-isopropylidenecarbacyclin-11,15-ditetrahydropyranyl ether

Following the same procedure as in the above Preparative Example 1(e) except that 1.45 g of sodium hydride (55% dispersion in mineral oil), 64 ml of dimethyl sulfoxide, 9.3 g of triphenyl-4-carboxybutylphosphonium bromide and 1.47 g of the ketone prepared as described in the Preparative Example 6(d) were used, there was obtained 570 mg of the desired product as an oily substance and 334 mg of the 5Z isomer thereof.

5E isomer:
infrared absorption spectrum (liq) $v_{max}$ cm$^{-1}$: 1020, 1710, 1740.

5Z Isomer
infrared absorption spectrum (liq) $v_{max}$ cm$^{-1}$: 1020, 1710, 1740.

(f) 16-methyl-20-isopropylidenecarbacyclin

Following the same procedure as in the above Preparative Example 1(f), except that there was employed 540 mg of the dipyranyl compound prepared as described in the Preparative Example 6(e), there was obtained 223 mg of the desired product as an oily substance.

infrared absorption spectrum (liq) $v_{max}$ cm$^{-1}$: 970, 1704, 3350.

nuclear magnetic resonance spectrum (CDCl$_3$) δppm: 0.88 (3H, multiplet); 1.60 (3H, singlet); 1.69 (3H, singlet); 3.80 (2H, broad); 4.8–5.6 (4H, multiplet).

An example of the pharmaceutical compositions of this invention is now given.

PHARMACEUTICAL COMPOSITION

Capsules

In 20 g of ethanol, 20 mg of the compound of Preparative Example 1 was dissolved, and well mixed with 100 g of lactose. Ethanol was distilled off under reduced pressure, and the resulting lactose mixture was used to fill 100 mg-hard capsules (containing the active ingredient at around 0.02%) to give capsule preparations. If necessary, a little lubricant such as magnesium stearate may be employed.

We claim:
1. A carbacyclin derivative of the formula:

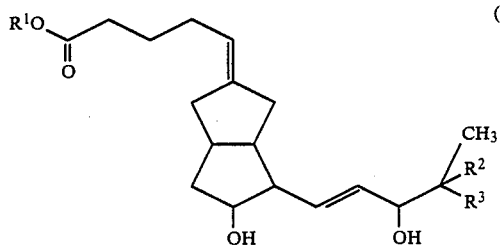

(I)

wherein R$^1$ is hydrogen or C$_1$–C$_{10}$ alkyl; R$^2$ is hydrogen or methyl; and R$^3$ is 3-butenyl or 4-pentenyl, or a pharmaceutically acceptable salt thereof.

2. The carbacyclin derivative of claim 1, wherein R$^1$ is hydrogen or methyl.

3. The carbacyclin derivative of claim 1, wherein R$^2$ is methyl.

4. The carbacyclin derivative of claim 1, wherein R$^3$ is 3-butenyl.

5. The carbacyclin derivative of claim 1, wherein R$^3$ is 4-pentenyl.

6. The carbacyclin derivative of claim 3, wherein R$^3$ is 4-pentenyl.

7. The carbacyclin derivative of claim 1, which is a compound of the formula (Ia):

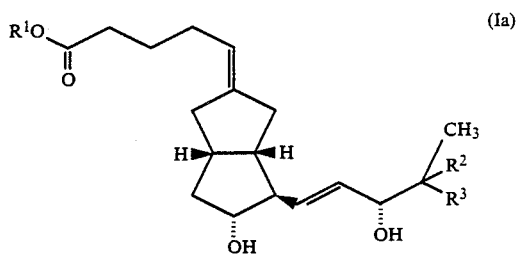

(Ia)

or a pharmaceutically acceptable salt thereof.

8. 16,16-dimethyl-19,20-didehydrocarbacyclin, or a pharmaceutically acceptable salt thereof.

9. 16-methyl-20-methylenecarbacyclin, or a pharmaceutically acceptable salt thereof.

10. 16,16-dimethyl-20-methylenecarbacyclin, or a pharmaceutically acceptable salt thereof.

11. 16,16-dimethyl-20-methylenecarbacyclin methyl ester.

12. A method for the treatment of ulcers in a human suffering from ulcers, comprising administering to said human an effective amount of a carbacyclin derivative of the formula (I):

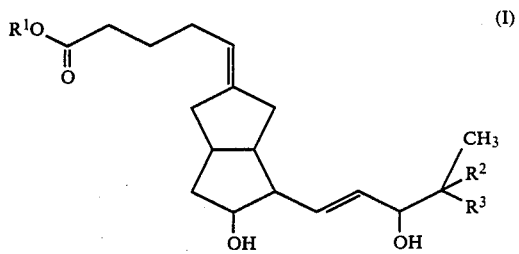

(I)

wherein R$^1$ is hydrogen or C$_1$–C$_{10}$ alkyl; R$^2$ is hydrogen or methyl; and R$^3$ is 3-butenyl or 4-pentenyl, or a pharmaceutically acceptable salt thereof.

13. The method of claim 12, wherein R$^1$ is hydrogen or methyl.

14. The method of claim 12, wherein R$^2$ is methyl.

15. The method of claim 12, wherein R$^3$ is 3-butenyl.

16. The method of claim 12, wherein R$^3$ is 4-pentenyl.

17. The method of claim 12, wherein R$^2$ is methyl and R$^3$ is 3-butenyl.

18. The method of claim 12, wherein R$^2$ is methyl and R$^3$ is 4-pentenyl.

19. The method of claim 12, wherein the carbacyclic derivative is a compound of the formula (Ia):

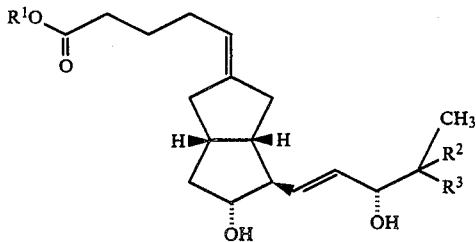

or a pharmaceutically acceptable salt thereof.

20. The method of claim 12, wherein the carbacyclin derivative is selected from the group consisting of:
16,16-dimethyl-19,20-didehydrocarbacyclin, and pharmaceutically acceptable salts thereof,
16-methyl-20-methylenecarbacyclin, and pharmaceutically acceptable salts thereof,
16,16-dimethyl-20-methylenecarbacyclin, and pharmaceutically acceptable salts thereof, and
16,16-dimethyl-20-methylenecarbacyclin methyl ester.

21. A pharmaceutical composition comprising an anti-ulcer compound in an amount effective for therapeutic and preventive treatment of ulcers, together with a pharmaceutically acceptable carrier, said anti-ulcer compound being a compound of the formula (I):

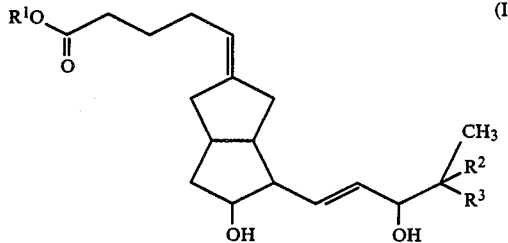

wherein $R^1$ is hydrogen or $C_1$–$C_{10}$ alkyl; $R^2$ is hydrogen or methyl; and $R^3$ is 3-butenyl or 4-pentenyl or a pharmaceutically acceptable salt thereof.

22. The composition of claim 21, wherein $R^1$ is hydrogen atom or methyl.

23. The composition of claim 21, wherein $R^2$ is methyl.

24. The composition of claim 21, wherein $R^3$ is 3-butenyl.

25. The composition of claim 21, wherein $R^3$ is 4-pentenyl.

26. The composition of claim 21, wherein $R^2$ is methyl and $R^3$ is 3-butenyl.

27. The composition of claim 21, wherein $R^2$ is methyl and $R^3$ is 4-pentenyl.

28. The composition of claim 21, wherein the carbacyclin derivative is a compound of the formula (Ia):

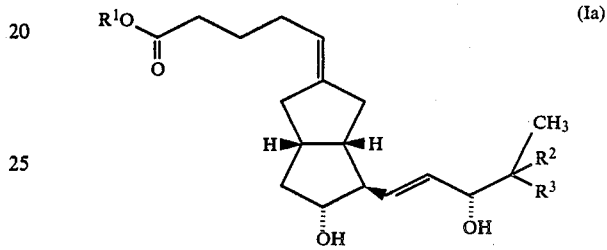

or a pharmaceutically acceptable salt thereof.

29. The composition of claim 21, wherein the carbacyclin derivative is selected from the group consisting of:
16,16-dimethyl-19,20-didehydrocarbacyclin, and pharmaceutically acceptable salts thereof,
16-methyl-20-methylenecarbacyclin, and pharmaceutically acceptable salts thereof,
16,16-dimethyl-20-methylenecarbacyclin, and pharmaceutically acceptable salts thereof, and
16,16-dimethyl-20-methylenecarbacyclin methyl ester.

* * * * *